United States Patent [19]

Kwak et al.

[11] Patent Number: 5,254,636
[45] Date of Patent: Oct. 19, 1993

[54] RAPID HYDROLYSIS OF CROSSLINKED MALEIC ANHYDRIDE/LOWER ALKYL VINYL ETHER COPOLYMERS

[75] Inventors: Yoon T. Kwak, Brooklyn, N.Y.; Stephen L. Kopolow, Plainsboro, N.J.

[73] Assignee: ISP Investments Inc., Wilmington, Del.

[21] Appl. No.: 889,341

[22] Filed: May 28, 1992

[51] Int. Cl.$^5$ ............ C08F 8/12; C08F 8/32; C08F 8/42; A61K 7/11

[52] U.S. Cl. .................... 525/369; 424/70; 424/71; 514/944; 525/379; 525/380; 525/384; 525/386; 526/271; 528/489; 528/499; 528/503

[58] Field of Search ............ 526/271; 525/369, 379

[56] References Cited

U.S. PATENT DOCUMENTS

| | | | |
|---|---|---|---|
| 4,874,604 | 10/1989 | Sramek | 424/47 |
| 4,952,558 | 8/1990 | Goertz | 526/271 |
| 5,024,779 | 6/1991 | Helioff | 252/162 |
| 5,032,391 | 7/1991 | Helioff | 424/71 |

Primary Examiner—Joseph L. Schofer
Assistant Examiner—Fred Zitomer
Attorney, Agent, or Firm—Marilyn J. Maue; Joshua J. Ward

[57] ABSTRACT

This invention relates to a process which significantly reduces the time for hydrolyzing a crosslinked maleic anhydride/lower alkyl vinyl ether copolymer to a clear gel which comprises suspending or dispersing fine granules of the crosslinked copolymer in deionized water and agitating the resulting dispersion or suspension for a period of between about 15 and about 130 minutes at a temperature of from about 60° to about 90° C. and then cooling the hydrolyzed mixture before introducing a basic neutralizing agent at a temperature of from about 15° to about 85° C. to produce a clear, homogeneous hydrolyzed gel having a Brookfield viscosity of from 5,000 to 250,000 cps.

14 Claims, No Drawings

RAPID HYDROLYSIS OF CROSSLINKED MALEIC ANHYDRIDE/LOWER ALKYL VINYL ETHER COPOLYMERS

In one aspect, the present invention relates to a more efficient, commercially feasible process for hydrolyzing crosslinked maleic anhydride/alkyl vinyl ether copolymers and in another aspect the invention relates to the formation of a uniformly clear hydrolyzed gel having superior stabilization properties and containing substantially no salt contaminant.

BACKGROUND OF THE INVENTION

Hydrolyzed crosslinked maleic acid methyl vinyl ether copolymers are much in demand as stabilizing agents for pharmaceutical and cosmetic formulations as described in U.S. Pat. Nos. 5,024,779 and 5,032,391. These hydrolyzed copolymers, because of their non-toxicity and stabilizing effects, also provide for controlled release of medicaments when incorporated into pharmaceutical compositions. Notwithstanding their importance, the preparation of a uniformly clear hydrolyzed maleic acid/alkyl vinyl ether cross-linked copolymer gel involves time consuming procedures similar to ageing which requires treatment of a hydrolysis mixture up to 24 hours in order to achieve a clear gel form. In many cases, the gels obtained have a hazy appearance and gel content is subject to variations in the extent of salt formation resulting from a secondary reaction between the maleic and amine components which causes a reduction in viscosity and which affects the clarity of the product. The conventional hydrolysis processes involve introducing copolymer into an aqueous base solution containing about 0.2-5.0 weight % of an organic amine neutralizer as shown in U.S. Pat. No. 5,024,779.

Accordingly, it is an object of this invention to provide a more economical and commercially feasible process for obtaining a uniformly clear gel of a hydrolyzed, crosslinked maleic acid/alkyl vinyl ether copolymer within the period of less than 150 minutes, and in most cases less than about 90 minutes.

Additionally, it is an object of this invention to provide a hydrolyzed maleic acid/methyl vinyl ether cross-linked copolymer gel containing substantially no salt contaminant.

Still another object of this invention is to produce a maleic acid/lower alkyl vinyl ether stabilizing gel having a high Brookfield viscosity.

These and many other objects of the invention will become apparent from the following description and disclosure.

THE INVENTION

In accordance with this invention there is provided a hydrolysis process which involves a critical sequence of steps in the production of a hydrolyzed, cross-linked maleic acid/$C_1$ to $C_4$ alkyl vinyl ether copolymer as a uniformly clear gel. This process concerns the treatment of a finely particulate cross-linked maleic anhydride/alkyl vinyl ether copolymer having a monomer weight ratio of between about 1:1 and about 1:2, more often between about 1:1.05 and about 1:1.2, and having an average particle size of from about 1 micron to about 1500 microns, preferably 100 to about 800 microns or in the form of a fine powder. The cross-linked copolymers of this invention are those of high molecular weights greater than 1,000,000 and Brookfield viscosities between about 45,000 and about 150,000 cps. A particularly preferred species is the cross-linked maleic anhydride/methyl vinyl ether copolymer, such as STABILEZE®, available from International Specialty Products; although other cross-linked maleic anhydride/lower alkyl vinyl ether copolymers are also suitably employed in this invention. In certain cases, where the average particle size exceeds the above limit, the cross-linked copolymer can be subjected to micropulverization before use. Various grades of STABILEZE are available, i.e. the 06 type is 2.5% cross-linked, the 12 type is 2% cross-linked and the 15 type is 3-3.5% cross-linked.

The copolymers of the invention can be crosslinked with any of the conventional crosslinking agents, including terminally unsaturated dienes, e.g., 1,9-decadiene, 1,7-octadiene, and the like.

In the process of the present invention, the particulate, crosslinked copolymer is introduced into deionized water with constant agitation to form a uniform dispersion or suspension of between about 0.1 and about 2.0 weight % solids as is achieved with a weight ratio of copolymer to water of from about 1:10 and about 1:10,000, more desirably, between about 1:100 and about 1:1,000, to provide a dispersion of about 0.2-0.6 weight % solids.

The dispersion or suspension is then heated to a temperature of from about 60° to about 90° C., preferably from about 60° to about 80° C., with constant agitation over a period of from about 15 to about 130 minutes or for a period sufficient to insure completion of the hydrolysis reaction, as may be indicated by the formation of a translucent liquid. Temperatures significantly lower than 60° C., e.g. 40° C. are not used because the required hydrolysis reaction time is inordinately increased, thus removing one of the advantages of the present process. Generally, it is recommended that with larger particles of crosslinked copolymer, e.g. above about 850 microns, hydrolysis temperatures within the upper portion of the above range, e.g. above 65° C., be employed to shorten the reaction time. When premixing of copolymer and water is not employed, the cross-linked copolymer can be directly introduced into the deionized water maintained at the desired reaction temperature with constant agitation to form the translucent hydrolyzed, acidic liquid product. It is critical that no basic neutralizer be present during this hydrolysis step.

After the hydrolysis is completed, the liquid mixture is allowed to cool, or is cooled to below the hydrolysis temperature, preferably to at least 5° below the hydrolysis temperature, by the addition of cool water. Typically cooling to a temperature of between about 15° and about 80° C., preferably between about 25° and about 65° C., is recommended. At this point a basic neutralizer is added and thoroughly mixed into the hydrolyzed liquid over a period of from about 1 to 12 minutes to provide the uniform, clear gel having a Brookfield viscosity within the range of from about 5,000 to about 250,000, more desirably between about 40,000 and 130,000 cps and containing substantially no salt contaminant.

Alternatively, the hydrolysis and cooling process can be carried out by using only a portion, e.g. a halfportion, of the water requirement for hydrolyzing the dispersed or suspended particles and the remaining portion for cooling the reaction mixture before introduction of the neutralizing agent.

Any basic neutralizer can be employed in this invention, species of which include organic and inorganic bases. For example, sodium, potassium and ammonium hydroxides can be employed as well as organic amines, alkanolamines and glycinate esters such as mono-, di- or tri- ethanol amines, aminomethyl propanol, aminomethyl propanediol, tris(hydroxymethyl)amino methane, tetrahydroxypropyl ethylenediamine, sodium hydroxymethyl glycinate, polyethylene glycol cocamine, triethylamine, triamylamine, etc. The base component employed is added in an amount of from about 0.4 to about 5 parts per part of hydrolyzed, crosslinked copolymer depending on the basic component used. Generally, the amount of ammonium, sodium or potassium hydroxides is used in an amount of at least 1.5 parts per part of polymer, as opposed to organic bases which are generally employed in lower amounts. The neutralizer stabilizes the hydrolyzed mixture to provide a clear gel having a pH of between about 5 and about 8 which contains substantially no salt contaminant. The neutralizing agent is usually added as a 95 to 50 weight % aqueous solution.

The clear hydrolyzed crosslinked copolymer of this invention is formed immediately upon contact with the neutralizer so that laborious hours of mixing and digesting formerly required are eliminated. Additionally, by the present process, the formation of organic salt monomer is avoided so that the product is achieved in a high state of purity Finally, the prehydrolysis step allows for increased solids content in the gel product obtained such that a 2 to about 7% solids in the gel can be recovered as the clear gel product of the process.

Having thus described the invention, reference is now had to the accompanying examples which provide preferred and comparative procedures in the formation of the present gel products. These examples are not to be construed as limiting to the scope of the invention which is more broadly described above and in the appended claims.

EXAMPLE I

One gram of STABILEZE ® 06* was added to 197 g. of deionized water at 80° C. with constant stirring and agitation continued for about 20 minutes. A translucent liquid developed which indicates that the dispersed, crosslinked copolymer (pH 2.5) was hydrolyzed.

* maleic anhydride/methyl vinyl ether (1:1) copolymer 2.5% crosslinked with 1,9-decadiene and having a Brookfield viscosity (TE spindle, 10 rpm) of 70,000-90,000 cps.

The dispersion was cooled to 60° C. and then a 50% aqueous solution of 2.0 g. of triethanolamine was added. A homogeneous clear gel of the hydrolyzed, crosslinked copolymer was obtained within 1 minute.

Agitation was continued for an additional ten minutes to insure uniform distribution of the amine.

The resulting clear gel product had a pH of 7.1 and a Brookfield viscosity of 117,000 cps.

EXAMPLE II

Example 1 was repeated, except that aminomethyl propanediol was substituted for triethanolamine. The results of this experiment in the formation of a clear gel within one minute of contact with the diol, simulated that in Example I. The pH of this gel product was 6.88 and the Brookfield viscosity was 99,000 cps.

EXAMPLE III

Example I was repeated, except that tris(hydroxymethyl) aminomethane was substituted for triethanolamine. The results of this experiment in the formation of a clear gel within one minute of contact with the present base, simulated that in Example I. The pH of this gel product was 6.82 and the Brookfield viscosity was 100,000 cps.

EXAMPLE IV

Example I was repeated, except that tetrahydroxy propyl ethylenediamine was substituted for triethanol amine. The results of this experiment in the formation of a clear gel within one minute of contact with the present base simulated that in Example I. The pH of this gel product was 6.83 and the Brookfield viscosity was 111,000 cps.

EXAMPLE V

Example I was repeated, except that diethanolamine was substituted for triethanolamine. The results of this experiment in the formation of a clear gel within one minute of contact with the present base simulated that in Example I. The pH of this product was 6.92 and the Brookfield viscosity was 103,000 cps.

COMPARATIVE EXAMPLE VI

One gram of STABILEZE ® 06 was added to 170 g. of deionized water containing 1 g. of triethanolamine at 80° C. with constant stirring, and agitation was continued for about 35 minutes. Since the dispersion remained milky, the mixture was agitated for an additional 5.5 hours, after which a hazy gel was obtained as the final product.

COMPARATIVE EXAMPLES VII-X

Repetitions of Example VI were carried out with the substitution of each of the bases: aminomethylpropanediol, tris(hydroxymethyl) aminomethane, tetrahydroxypropyl ethylenediamine and diethanolamine. These experiments resulted in the same hazy gel product after 6-8 hours of agitation at about 80° C. as was obtained in Example VI.

EXAMPLE XI

Example I was repeated except that 0.8 g. aminomethylpropanediol was substituted for triethanolamine. A clear gel was formed within one minute of contact with this base. The gel product had a pH of 7.86 and a Brookfield viscosity of 101,000 cps.

EXAMPLE XII

Example I was repeated except that 0.6 g. of monoethanolamine was substituted for triethanolamine. A clear gel was formed within one minute of contact with this base. The gel product had a pH of 8.42 and a Brookfield viscosity of 94,250 cps.

EXAMPLE XIII

In a glass beaker, 1 g. of STABILEZE ® 06 was agitated with 99 g. of deionized water at 80° C. for 40 minutes, after which the resulting hydrolyzed translucent product solution was cooled 60° C. by the addition of 97.0 g. cool water. Then 2.0 g. of triethanolamine (50% aqueous solution) was added with agitation. A clear gel was obtained within one minute of contact with the base. The gel product had a pH of 6.70 and a Brookfield viscosity of 98,500 cps.

EXAMPLE XIV

Example I was repeated except that 4.0 g. KOH in 10% aqueous solution was substituted for triethanol amine. A clear gel was formed within one minute of contact with KOH solution. The gel product had a pH of 6.53 and a Brookfield viscosity of 108,000 cps. Similar results were obtained with 10% NaOH.

EXAMPLE XV

Example I was repeated except that 2.0 g. $NH_4OH$ 30% aqueous solution was substituted for triethanolamine. A clear gel formed within one minute of contact with $NH_4OH$ solution. The gel product had a pH of 6.53 and a Brookfield viscosity of 107,000 cps.

EXAMPLE XVI

Example I was repeated except that Suttocide A (sodium hydroxymethyl glycinate) was substituted for triethanolamine and a STABILEZE® 06 hydrolysis solution of 0.5% solids was employed. A clear gel was formed within one minute of contact with this base. The gel product had a pH of 6.50 and a Brookfield viscosity of 103,000 cps.

What is claimed is:

1. The process for rapid hydrolysis of crosslinked maleic anhydride/$C_1$ to $C_4$ alkyl vinyl ether copolymer particles having an average particle size of from about 1 to about 1500 microns to form a clear gel which comprises (a) agitating said crosslinked copolymer in between about 10 to about 10,000 parts of deionized water to form a suspension or dispersion; (b) hydrolyzing the copolymer at a hydrolysis temperature of from about 60° to about 90° C. for a period sufficient to complete hydrolysis of the crosslinked copolymer; (c) cooling the reaction mixture to at least 5° below the hydrolysis temperature and (d) then adding between about 0.4 and about 5 weight % based on copolymer of a basic neutralizing agent to provide a clear stabilized gel.

2. The process of claim 1 wherein said crosslinked copolymer particles have an average particle size of from about 100 to about 800 microns.

3. The process of claim 1 wherein said cross-linked copolymer is in the form of a micropulverized powder.

4. The process of claim 1 wherein said copolymer prior to hydrolysis is a crosslinked maleic anhydride/methyl vinyl ether copolymer having a Brookfield viscosity between about 50,000 and about 150,000 cps.

5. The process of claim 4 wherein said copolymer prior to hydrolysis has a Brookfield viscosity of between about 70,000 and about 90,000 cps.

6. The process of claim 1 wherein the particle size of the copolymer is above 150 microns and the hydrolysis temperature is above 70° C.

7. The process of claim 1 wherein the particle size of the copolymer is between about 1 and about 100 microns and the hydrolysis temperature is between about 60° and about 70° C.

8. The process of any one of claims 1 through 6 wherein said basic neutralizing agent is selected from the group of inorganic hydroxides, amines, alkanolamines and glycinate esters.

9. The process of claim 1 wherein the hydrolyzed mixture is cooled to between about 15° and about 80° C. and at least 5° below the hydrolysis temperature.

10. The process of claim 9 wherein the hydrolysis temperature is between about 60° and about 80° C. and the hydrolyzed mixture is cooled to between about 25° and about 65° and at least 5° below the hydrolysis temperature.

11. The process of claim 1 wherein the mixture of copolymer and deionized water is a dispersion of 0.1 to 2 weight % so ids.

12. The process of claim 11 wherein the mixture of copolymer and deionized water is a dispersion of 0.2 to 0.6 weight % solids.

13. The process of claim 1 wherein said basic neutralizing agent is an amine and the weight ratio of hydrolyzed copolymer to amine is between about 1:0.4 and about 1:1.8.

14. The process of claim 1 wherein said basic neutralizing agent is sodium, potassium or ammonium hydroxide and the weight ratio of hydrolyzed copolymer to hydroxide is between about 1:1.8 and about 1:4.2.

* * * * *